US012660995B2

(12) United States Patent
Duckett, III

(10) Patent No.: US 12,660,995 B2
(45) Date of Patent: Jun. 23, 2026

(54) SINGLE CHIP CAMERA HEAD FOR MULTI-SPECTRAL IMAGING AND METHODS OF USING THE SAME

(71) Applicant: KARL STORZ IMAGING, INC., Goleta, CA (US)

(72) Inventor: George E. Duckett, III, Castaic, CA (US)

( * ) Notice: Subject to any disclaimer, the term of this patent is extended or adjusted under 35 U.S.C. 154(b) by 354 days.

(21) Appl. No.: 18/241,661

(22) Filed: Sep. 1, 2023

(65) Prior Publication Data

US 2025/0072739 A1 Mar. 6, 2025

(51) Int. Cl.
| *A61B 1/06* | (2006.01) |
| *A61B 1/00* | (2006.01) |
| *A61B 1/04* | (2006.01) |

(52) U.S. Cl.
CPC ........ *A61B 1/0638* (2013.01); *A61B 1/00096* (2013.01); *A61B 1/00186* (2013.01); *A61B 1/043* (2013.01); *A61B 1/046* (2022.02)

(58) Field of Classification Search
CPC .......................... G02B 23/2461; G02B 23/243
See application file for complete search history.

(56) References Cited

U.S. PATENT DOCUMENTS

| 9,258,468 B2* | 2/2016 | Cotton | ................... G01J 3/0264 |
| 9,258,549 B2* | 2/2016 | DiCarlo | ............... A61B 1/0646 |
| 10,606,062 B2 | 3/2020 | Duckett, III et al. | |
| 12,220,108 B2* | 2/2025 | Otani | ........................ A61B 1/07 |
| 2007/0153542 A1* | 7/2007 | Gono | ..................... A61B 1/063 |
| | | | 362/574 |
| 2010/0245616 A1* | 9/2010 | Yoshino | ............... A61B 1/0646 |
| | | | 382/163 |
| 2012/0253157 A1* | 10/2012 | Yamaguchi | .......... A61B 1/0646 |
| | | | 600/328 |
| 2013/0041221 A1* | 2/2013 | McDowall | ............. H04N 23/56 |
| | | | 348/E9.037 |
| 2016/0317003 A1* | 11/2016 | Ogata | ................. G02B 23/2484 |
| 2018/0000334 A1* | 1/2018 | Morishita | ............ A61B 1/0646 |
| 2020/0150041 A1* | 5/2020 | Harootunian | ...... G01N 21/6456 |
| 2021/0267443 A1* | 9/2021 | Baumann | ............... H04N 25/61 |

OTHER PUBLICATIONS

Hemb, B., Extended European Search Report, European Patent Office, Jan. 3, 2025, pp. 1-9, European Patent Office, Munich.

* cited by examiner

*Primary Examiner* — John P Leubecker
(74) *Attorney, Agent, or Firm* — David N. Villalpando; Jason Worgull; Jacqueline Cohen

(57) ABSTRACT

Methods and systems are provided to enable multiple imaging modalities with a single camera head. The camera head may include a single chip system capable of measuring different wavelengths of light on different regions of the same image sensor to generate different images. The light source in the system can adjust the output spectra by using a plurality of illuminants and filters, and measurements from different light channels from different regions of the image sensor can be used to generate white light images, fluorescence image, perfusion images, fluorescein images, and the like.

25 Claims, 9 Drawing Sheets

SINGLE CHIP CAMERA HEAD FOR MULTI-SPECTRAL IMAGING AND METHODS OF USING THE SAME

BACKGROUND

During the course of a surgery or surgical procedure, one or more images of a surgical site may be captured. The imaging may enable a surgeon to view the surgical site and make determinations based on the imaging. For example, the surgeon may use images or a live feed of a surgical site in maneuvering a surgical tool or to make a visual diagnosis, take a biopsy, etc. Different imaging modalities may be used during the surgery or surgical procedure for different purposes, with each modality providing a different view or a different set of information about the surgical site.

Camera heads, usually connected to imaging scopes, such as endoscopes or exoscopes, can provide imaging modalities, such as white light imaging and fluorescence imaging, but are limited in the number of different imaging modalities that can be simultaneously provided. Further, some such imaging modalities require complex temporal synchronization between the camera head and the corresponding light source to accurately capture the image information required for a given modality, which will usually result in a reduction of the effective frame rate for a given modality. For example, common fluorescence imaging (FI) techniques require a strobing of the light source between a white light illumination and a fluorescence excitation light illumination. Each frame displayed combines a first collected white light frame with a subsequently collected FI frame (appropriately processed) to create an overlay of the two images. This process necessarily reduces the possible displayed frame rate by at least 50%.

Camera heads can also include multiple complex or specialized image sensor combinations; however, these complicated sensor systems result in a corresponding increase in cost. For example, some FI techniques may require that the camera head employ two separate image sensors in order to generate the two separate images that are overlaid by an image processor. In such an example, one of the images sensors may require infrared detection capabilities. As a result, the cost of the camera head increases due to the need for an additional, specialized sensor to generate the FI image. The additional optics that may be needed to further direct light to the second sensor which can also increase the cost associated with design and manufacture of such multiple-chip FI capable camera heads.

SUMMARY

The shortcomings of systems discussed above can be addressed with the systems and methods disclosed herein. By providing a light source with a plurality of individual illuminants, and one or more possible optical filters, different wavelengths of light can be output by the light source corresponding to the requirements of the current imaging modality. Moreover, different imaging modalities can be enabled by providing a single chip camera head discussed herein. The camera head includes a single image sensor chip that receives separated, transmitted light into distinct, separate regions on the single image sensor, such that light received from the surgical scene can be processed in accordance with the selected imaging modality, without needing to use a different camera head. The imaging sensor may comprise a color filter array (CFAs), such as a Bayer array, capable of capturing data at various spectral bands (e.g., ranges of wavelengths) of light. Various color channels of the image sensor may be processed to generate images in the various modalities.

The camera heads may beneficially enable a physician, during the course of the surgery or surgical procedure, to alternate between different imaging modes to capture different images of the surgical scene. For example, the physician may be able to begin in a white light mode and capture a white light image of the surgical scene, and then transition the imaging system into an oxygenation mode to generate a perfusion image to examine how blood is flowing in the surgical site without needing to switch out the camera head. Additionally, image processing can use that data from the image sensor to produce false colored overlays of fluorescence images over visible light images, which can be beneficial in performing various surgeries and diagnoses. The use of the single camera head also beneficially reduces cost and time needed to conduct the surgery or surgical procedure.

The camera heads according to embodiments of the present disclosure enable various imaging modalities to be generated from a single image sensor, which can greatly reduce the cost of the camera head over more conventional multi-chip systems. For example, the camera head may be manufactured to include only the single image sensor while omitting additional image sensors. Eliminating the need for multiple image sensors may reduce the overall cost associated with the manufacturing process in fabricating the camera head, as well as the price of the camera head to the consumer. It should be noted that the camera head may be manufactured with multiple image sensors, however a single image sensor alone is utilized to capture the various imaging modalities discussed herein. In such embodiments, additional image sensors may be utilized to perform other tasks, such as providing additional image data which can be used to generate high dynamic range (HDR) or extended depth of field images for display.

DETAILED DESCRIPTION

The exemplary systems and methods of this disclosure will be described in relation to imaging. However, to avoid unnecessarily obscuring the present disclosure, the description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

Figure 1:
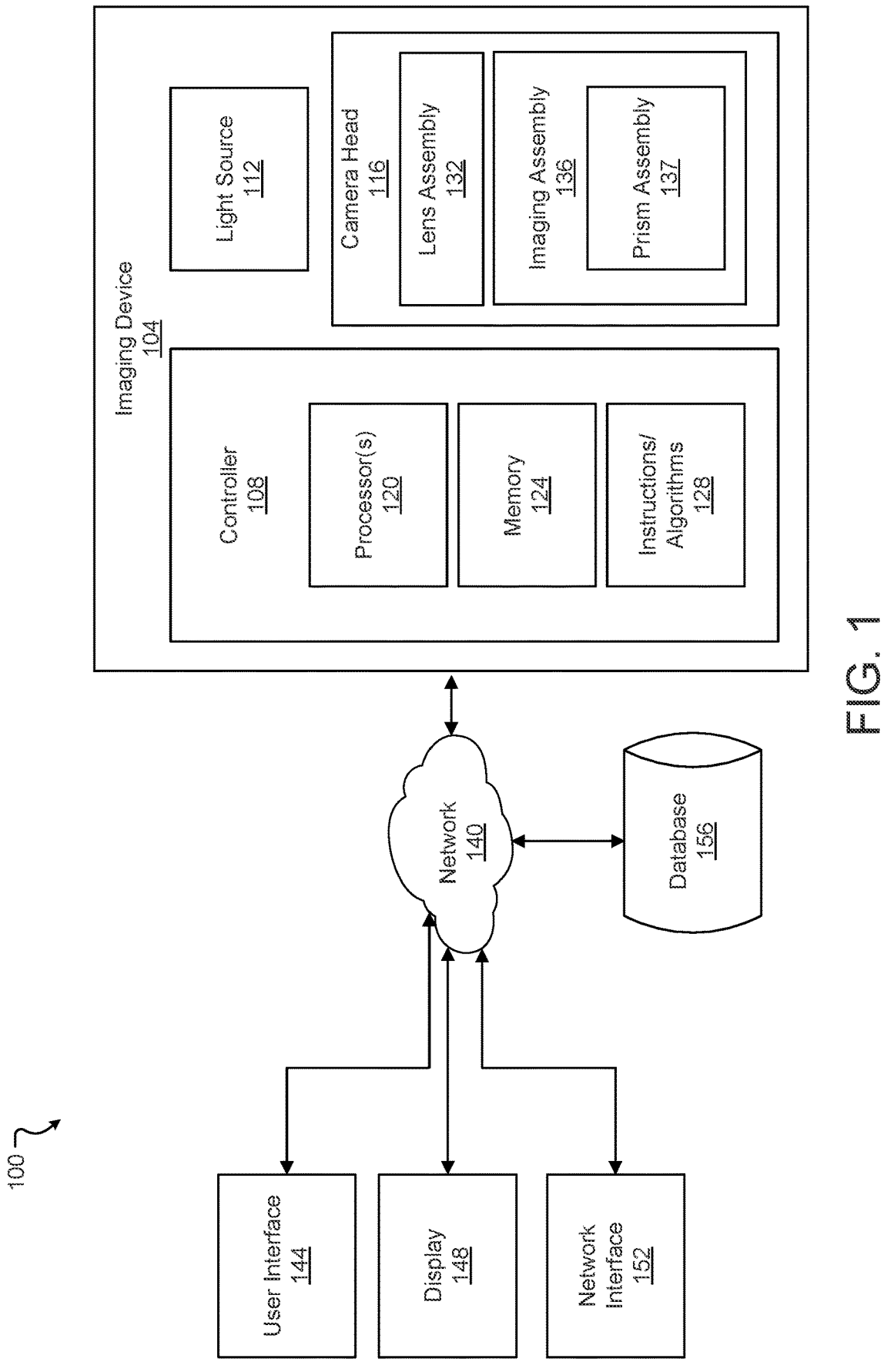
FIG. 1 shows a block diagram of a system according to at least one exemplary embodiment.

Turning first to FIG. 1, aspects of a system 100 are shown according to at least one exemplary embodiment. The system 100 includes an imaging device 104, a network 140, a user interface 144, a display 148, a network interface 152. In some embodiments, the system 100 may include additional or alternative components, and the components illustrated in FIG. 1 are in no way limiting. For example, the system 100 may include additional or alternative imaging devices, additional surgical tools (e.g., surgical drills, endoscopes, etc.), combinations thereof, and the like. As another example, a controller 108 disposed in the imaging device 104 may alternatively be disposed outside of the imaging device 104 and may communicate with the imaging device 104 (or components thereof) wirelessly and/or through a wired connection. Such an external controller may be comprised in a camera control unit (CCU).

The imaging device 104 may be capable of capturing one or more images by illuminating a surgical scene with, for example, the light source 112. The light source 112 may provide a continuous illumination that reflects, scatters, and/or causes fluorescent emission from elements of the surgical scene, and such light is captured by a camera head 116. Often between the camera head and the surgical scene will be an intermediate device, such as an endoscope, borescope (for industrial applications), or optical elements of an exoscope, which capture light from the scene and may condition and relay it to the camera head 116. It should be noted that light collected from an imaging scene will be referred to throughout as being "reflected" off or from a surgical scene, however, it should be understood that this "reflected" light from an image scene includes all light gathered by imaging optics and passed to the camera head 116. Thus this "reflected" includes light reflected from elements of the scene, light scattered from surfaces, fluorescent light emitted from fluorophores, light directly coming from other illumination sources, etc.

The camera head 116 may be a device containing a lens assembly 132 and an imaging assembly 136 that measures the received light that has been reflected from the surgical scene. The imaging assembly 136 comprises a prism assembly 137 and one or more image sensors. The lens assembly 132 may include a plurality of optical components that condition and/or direct light received from the surgical scene into the prism assembly 137. The one or more image sensors of the imaging assembly 136 measure the captured light, with these measurements used by the controller 108 to generate one or more images of the surgical scene. While some embodiments discussed herein reference a single image sensor, it is to be understood that other embodiments may comprise a plurality of additional image sensors dedicated to other imaging modalities not discussed herein, and that the number of image sensors present or available is in no way limited.

The processor 120 may provide processing functionality and may correspond to one or many computer processing devices. For instance, the processor 120 may be provided as a Field Programmable Gate Array (FPGA), an Application-Specific Integrated Circuit (ASIC), any other type of Integrated Circuit (IC) chip, a collection of IC chips, a microcontroller, a collection of microcontrollers, a GPU(s), or the like. As another example, the processor 120 may be provided as a microprocessor, Central Processing Unit (CPU), Graphics Processing Unit (GPU), and/or plurality of microprocessors that are configured to execute the instructions or algorithms 128 and/or data stored in memory 124. The processor 120 enables various functions of the system 100 upon executing the instructions or algorithms 128 and/or data stored in the memory 124.

The memory 124 may be or comprise a computer readable medium including instructions that are executable by the controller 108 and/or the processor 120. The memory 124 may include any type of computer memory device and may be volatile or non-volatile in nature. In some embodiments, the memory 124 may include a plurality of different memory devices. Non-limiting examples of memory 124 include Random Access Memory (RAM), Read Only Memory (ROM), flash memory, Electronically-Erasable Programmable ROM (EEPROM), Dynamic RAM (DRAM), etc. The memory 124 may include instructions that enable the controller 108 to control the various elements of the system 100 and to store data, for example, into the database 156 and retrieve information from the database 156. The memory 124 may be local (e.g., integrated with) the imaging device 104 or separate from the imaging device 104.

The instructions 128 comprise computer-readable software that is executable by the controller 108 and/or the processor 120 that cause the controller 108 and/or the processor 120 to perform one or more functions. The instructions 128 may, when processed by the processor 120, cause the processor 120 to perform one or more algorithms for image processing, for controlling one or more components of the system 100, combinations thereof, and the like. As an example, the instructions 128 may cause the processor to perform one or more image processing techniques (e.g., edge detection techniques, interpolations, demosaicing algorithms, Bayer filter pattern algorithms, image overlays, etc.) to convert measurements from the one or more image sensors into one or more images for storage and/or display.

The user interface 144 includes hardware and/or software that enables user input to the system 100 and/or any one or more components thereof. The user interface 144 may include a keyboard, a mouse, a touch-sensitive pad, touch-sensitive buttons, mechanical buttons, switches, and/or other control elements for providing user input to the system 100 to enable user control over certain functions of the system 100 (e.g., operating lighting and/or imaging capabilities of the imaging device 104, rendering processed video to the display 148, etc.). The user interface 144 may include buttons, switches, or other control means disposed on the imaging device 104 itself independent of or in addition to user interface controls not disposed in the imaging device 104. Simply as an illustrative example, the imaging device 104 and/or the display 148 may have input buttons and switches, and, additionally, a keyboard or mouse may be connected directly to the processor 120 (in embodiments where the processor 120 is disposed outside of the imaging device 104). All of these together constitute the user interface 144.

The display 148 may be or comprise a liquid crystal display (LCD), a light emitting diode (LED) display, a high definition (HD) display, a 4K display, or the like. The display 148 may be a stand-alone display or a display integrated as part of another device, such as a smart phone, a laptop, a tablet, a headset or head-worn device, and/or the like. In one embodiment, the display 148 may be a monitor or other viewing equipment disposed within an operating room, such that video feed captured from a surgery or surgical procedure can be rendered to the display 148 for a physician to view. In some embodiments, the display 148 may comprise a plurality of displays according to, for example, system design.

The network interface 152 may enable one or more components of the system 100 to communicate wired and/or wirelessly with one another or with components outside the system 100. These communication interfaces that permit the components of the system 100 to communicate using the network interface 152 include wired and/or wireless communication interfaces for exchanging data and control signals between one another. Examples of wired communication interfaces/connections include Ethernet connections, HDMI connections, connections that adhere to PCI/PCIe standards and SATA standards, and/or the like. Examples of wireless interfaces/connections include Wi-Fi connections, LTE connections, Bluetooth® connections, NFC connections, and/or the like.

The database 156 includes the same or similar structure as the memory 124 described above. In at least one exemplary embodiment, the database 156 is included in a remote server and stores video data captured during a surgery or surgical procedure (e.g., a camera on an endoscope capturing a live feed during an endoscopy).

Although FIG. 1 illustrates the various elements in the system 100 as being separate from one another, it should be appreciated that some or all of the elements may be integrated with each other if desired. For example, a single desktop or laptop computer or a CCU may include the processor 120, the memory 124, the user interface 144, and, optionally, the display 148. It should be further appreciated that each element in the system 100 includes one or more communication interfaces that enable communication with other elements in the system 100 over, for example, the network interface 152. Another example of a preferred embodiment of the system 100 includes an endoscope combined with the camera head 116 (or detachably connected thereto) with a built in user interface 144 that is connected to an external camera control unit (CCU), the CCU comprising the controller 108, the memory 124, the processor 120, the network interface 152, and a user interface 144, and the CCU is also connected such that it can output image data to the display 148.

Figure 2:
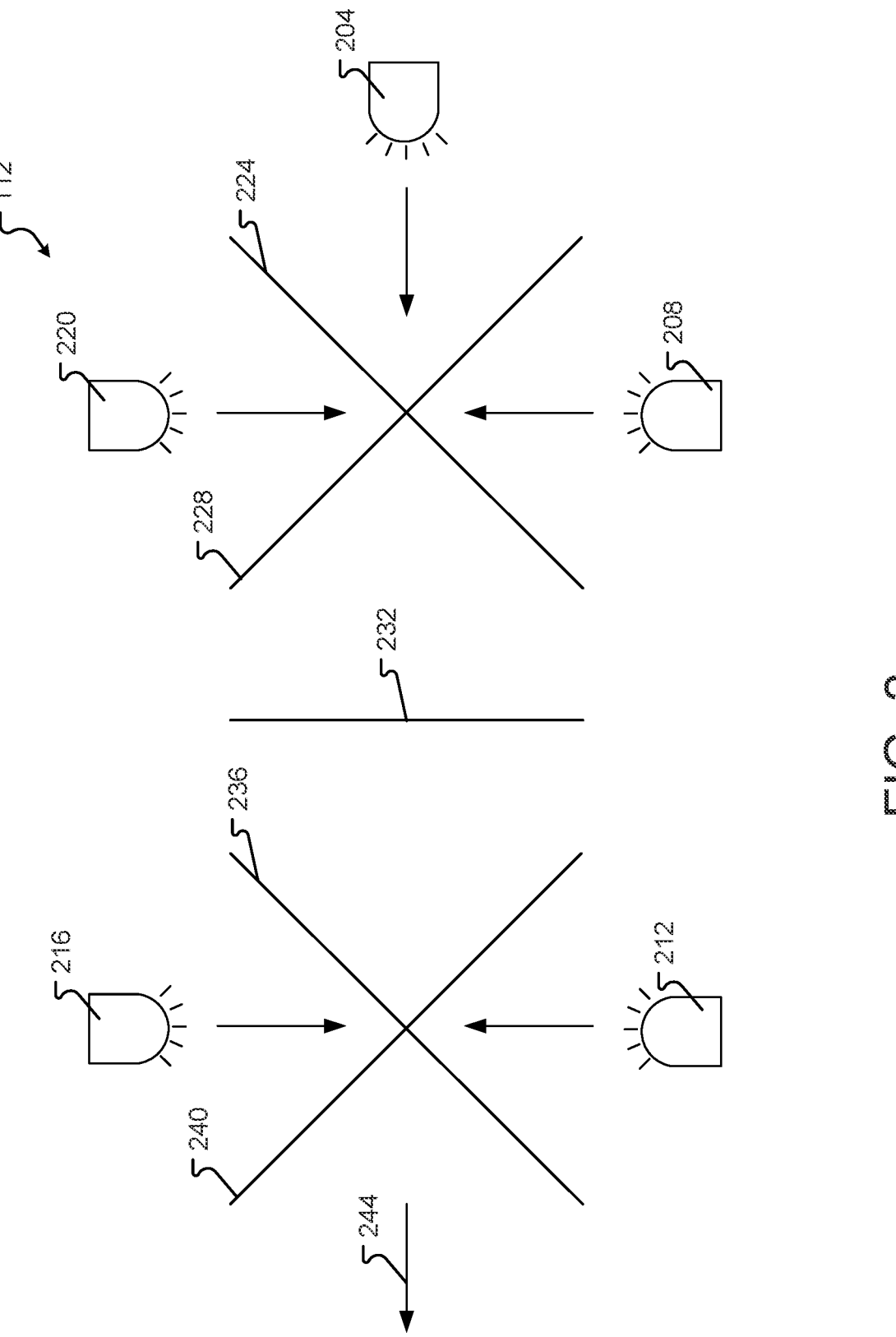
FIG. 2 shows a light source according to at least one exemplary embodiment.

FIG. 2 illustrates aspects of the light source 112 according to at least one exemplary embodiment of the present disclosure. The light source 112 may be or comprise an illumination device that includes a first illuminant 204, a second illuminant 208, a third illuminant 212, a fourth illuminant 216, and a fifth illuminant 220. Each of the illuminants may be capable of generating and/or emitting light at a set wavelength or a within a range of wavelengths. In one embodiment, the first illuminant 204 may generate green light (e.g., light with a central wavelength of about 550 nanometers (nm)) or, in some embodiments where a white light source is used, white light (e.g., light with wavelengths between 400 nm and 700 nm); the second illuminant 208 may generate blue light (e.g., light with a central wavelength of about 450 nm); the third illuminant 212 may generate infrared (IR) light with a wavelength of about 940 nm; the fourth illuminant 216 may generate infrared light with a wavelength of about 770 nm; and the fifth illuminant 220 may generate red light with a central wavelength of about 630 nm. The light generated by the illuminants may pass through a series of filters before being output from the light source 112, such that the final light output by the light source 112 includes a collection of the wavelengths generated by the separate illuminants. For example, a first filter 224 may reflect red light and transmit all other light, such that the red light generated by the fifth illuminant 220 is directed toward a third filter 232. Similarly, a second filter 228 may reflect light with wavelengths below 500 nm and transmit light with wavelengths above 500 nm. As a result, the second filter 228 may direct the blue light generated by the second illuminant 208 toward the third filter 232. The filtering parameters of the first filter 224 and the second filter 228 may enable the green light generated by the first illuminant 204 to pass through both the first filter 224 and the second filter 228 as the green light travels toward the third filter 232. This configuration of filters and illuminants allows for the precise selection of the spectral bands (also referred to herein as a set or range of wavelengths) in the resultant combined output light 244. Adjustment of the spectral values (e.g., wavelengths of light) of the illuminants and the filters of the light source can be done in order to correspond to the desired configuration of the imaging assembly 136 of the camera head 116, the particulars for various embodiments of which are described below.

As used herein and unless otherwise specified, the listing of the wavelengths of light include approximate wavelength values. For example, green light with a wavelength of 550 nm may also include, for example, a percentage variation thereof (e.g., 1% below and above the 550 nm value, 2% below and above the 550 nm value, 10% below and above the 550 nm value, 25% below and above the 550 nm value, etc.). Furthermore, the term "about" includes the percentage variation of the wavelength of light. For example, "about 550 nm" may encompass all wavelengths between 544.5 and 555.5 nm. In some embodiments, the listed wavelength of light may be a wavelength at which a broader spectrum or range of wavelengths constituting the light is centered. As an example, the green light with a wavelength of 550 nm may indicate that the green light includes a broad spectrum (e.g., range) of wavelengths between, say, 485 nm and 615 nm that is centered at 550 nm. As can be appreciated, such broad spectrums of wavelengths are not limited to green light, and other illumination sources discussed herein may similarly produce light with a broad spectrum of wavelengths. In some preferred embodiments, the light generated by different light sources may have overlapping spectra (e.g., ranges of wavelengths that overlap one another). In other words, the fifth illuminant 220 and the first illuminant 204 may both generate light that includes an overlapping range of wavelengths (e.g., overlapping wavelengths between 560 nm and 590 nm, overlapping wavelengths between 550 nm and 600 nm, etc.), and the first illuminant 204 and the second illuminant 208 may both generate light that includes an overlapping range of wavelengths (e.g., overlapping wavelengths between 480 nm and 550 nm, overlapping wavelengths between 450 nm and 580 nm, etc.). It is to be understood that these exemplary ranges, however, are no way limiting, and broader or narrow ranges of spectral overlap of light generated by different illuminants are possible.

The third filter 232 may operate to separate the visible light illuminants from the infrared illuminants by permitting light with wavelengths below 650 nm to pass therethrough, but reflecting light with wavelengths above 650 nm. As a result, the visible light generated and emitted by the first illuminant 204, the second illuminant 208, and/or the fifth illuminant 220 pass through the third filter 232, while any infrared light generated by the first illuminant 204, the second illuminant 208, and/or the fifth illuminant 220 is reflected. The placement of the third filter 232 may ensure that no infrared light that may be output from the first illuminant 204, the second illuminant 208, and/or the fifth illuminant 220 is an element of combined light output 244. A fourth filter 236 may reflect light with wavelengths between about 725 and 800 nm, while transmitting light of wavelengths shorter than 725 nm and greater than 800 nm. The fourth filter 236 directs the infrared light generated by the fourth illuminant 216 (which may be about 770 nm in wavelength) toward the exit of the light source 112. Similarly, a fifth filter 240 may reflect wavelengths of about 940 nm, while letting all other wavelengths pass therethrough; the fifth filter 240 ensures the infrared light generated by the third illuminant 212 (which may be about 940 nm in wavelength) is directed toward the exit of the light source 112. The fourth filter 236 and the fifth filter 240 permit visible wavelengths to pass therethrough and out of the light source 112. As shown in FIG. 2, the positioning of the first filter 224, the second filter 228, the third filter 232, the fourth filter 236, and the fifth filter 240 results in a combined light output 244 being output from the light source 112, with the combined light output 244 containing the wavelengths of light generated by each illuminant. In other words, the combined light output 244 may include two, three, or more spectrally distinct portions of light based on the number of illuminants active. As used herein, the term "spectrally distinct" means a different range, number, set, or content of wavelengths of light. In some cases, a first portion of light may overlap in spectral content with a second portion of light but may be considered spectrally distinct when the first portion of light contains spectral content (e.g., a set or range of wavelengths of light) that are not present in the second portion of light (or vice versa).

In some embodiments, the light source 112 may be strobed. In other words, the first illuminant 204, the second illuminant 208, the third illuminant 212, the fourth illuminant 216, and/or the fifth illuminant 220 may be modulated or duty cycled to periodically emit light, such that the combined light output 244 periodically illuminates the surgical site. In other embodiments, the light source 112 may not be strobed. In other words, the first illuminant 204, the second illuminant 208, the third illuminant 212, the fourth illuminant 216, and/or the fifth illuminant 220 may constantly generate light, such that the combined light output 244 illuminates the surgical site as long as the light source 112 remains on.

Figure 3A:
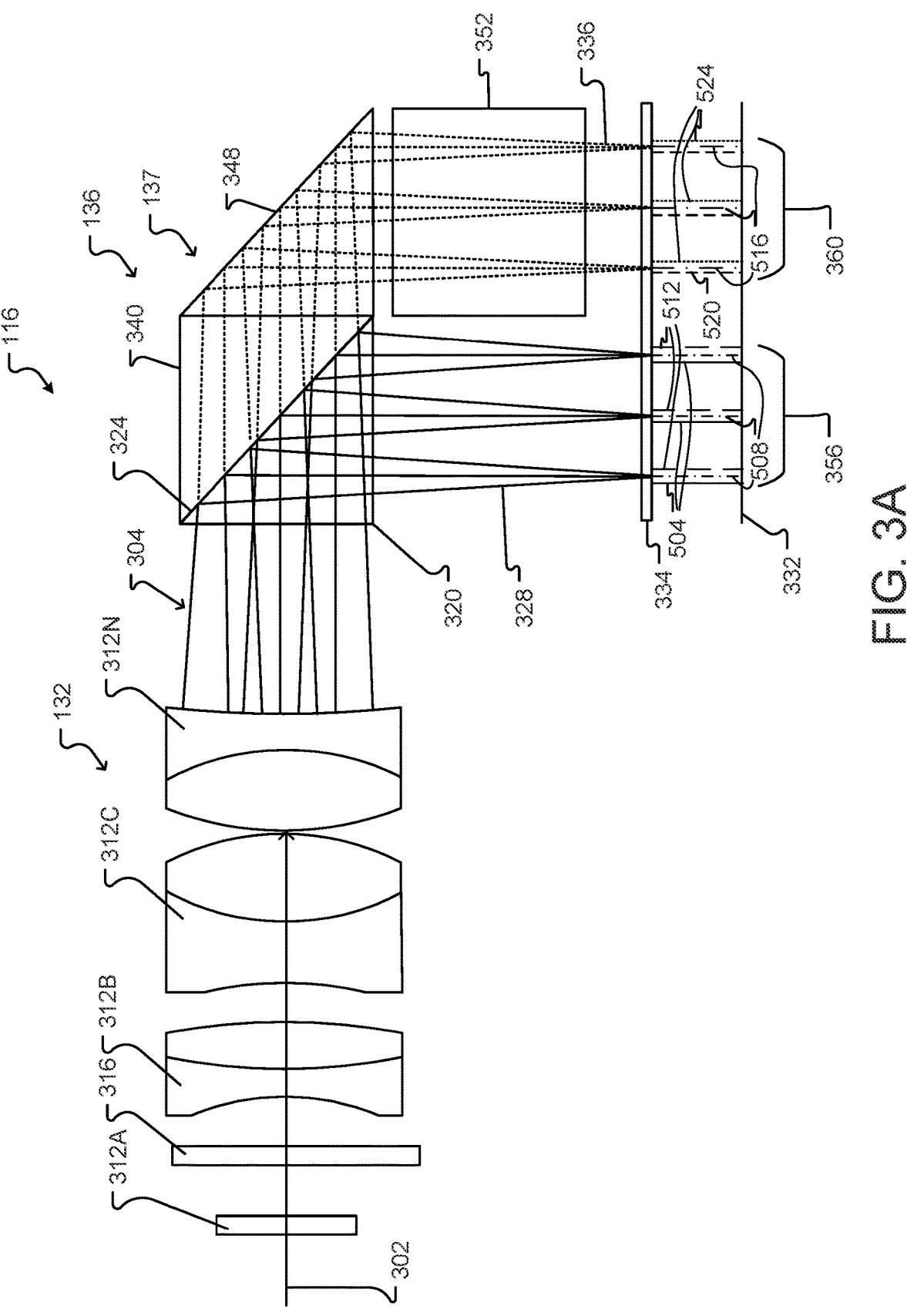
FIG. 3A shows a single chip imaging system according to at least one exemplary embodiment.
Figure 3B:
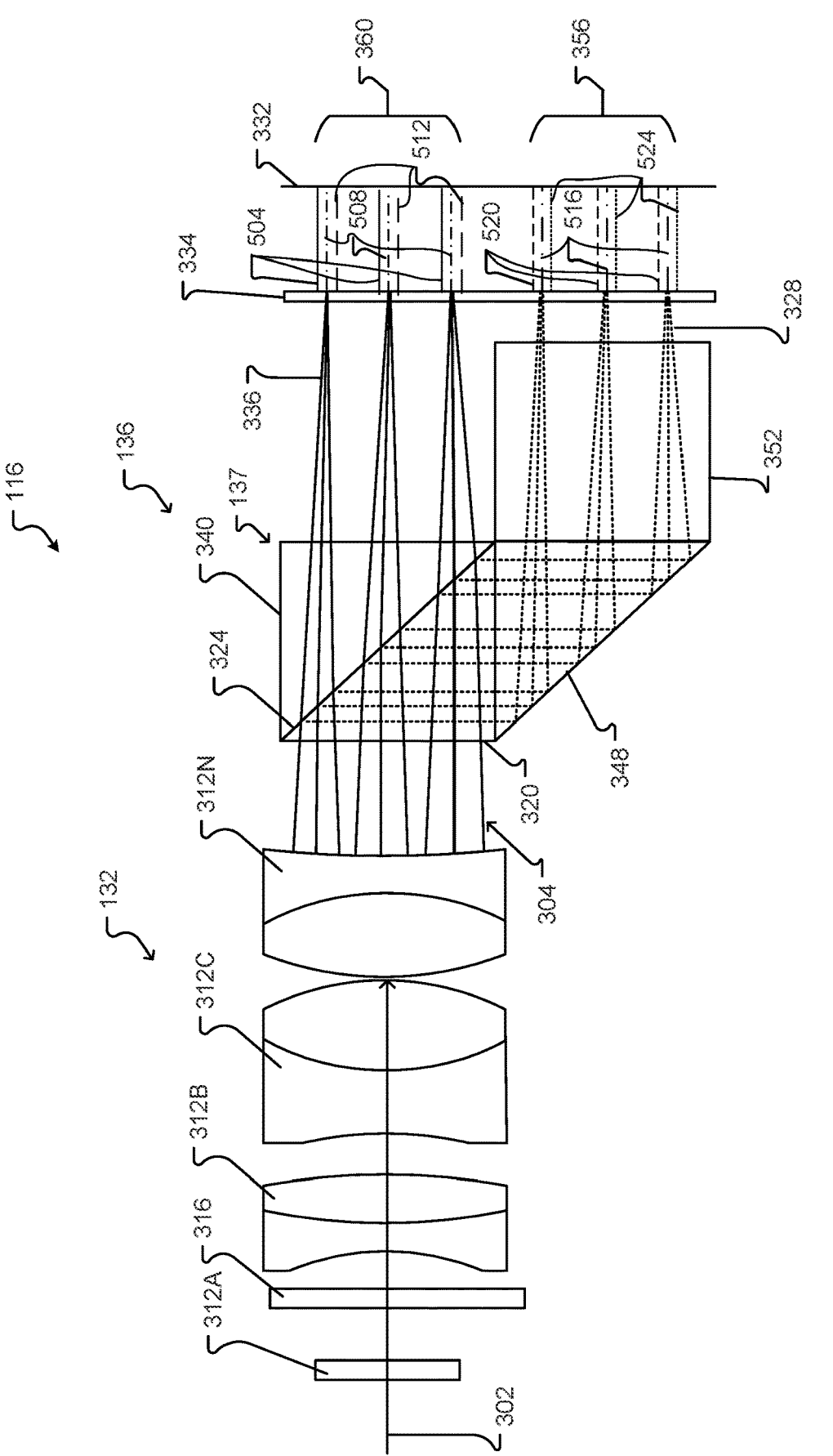
FIG. 3B shows an alternative single chip imaging system according to at least one exemplary embodiment.

FIGS. 3A-3B illustrate aspects of a camera head 116 according to at least one exemplary embodiment of the present disclosure. The camera head 116 includes a lens assembly 132 and an imaging assembly 136 including a prism assembly 137. The lens assembly 132 may include a collection of mirrors, lenses, filters, polarizers, and/or windows capable of conditioning and directing received light into the prism assembly 137. As shown in FIGS. 3A-3B, the lens assembly 132 includes a plurality of lenses 312A-312N and a first filter 316, which may direct the light 302 to the prism assembly 137. In some embodiments, the light 302 may be light reflected from a surgical scene and captured by the optics of an attached endoscope or those of an exoscope and be relayed or transmitted to the camera head 116. The first filter 316 may filter out one or more wavelengths of the light captured by the camera head 116. The first filter 316 may be a replaceable, selectable, or tunable filter, such that its characteristics may be selected depending on the requirements of the desired mode. For example, in one embodiment the first filter 316 may be a dichroic filter that passes light in a first range of wavelengths but rejects light in a second range of wavelengths. In a further embodiment, the first filter 316 may be a different dichroic filter that passes light from a third range of wavelengths and rejects light from a fourth range of wavelengths. Various particular implementations are discussed below. In one embodiment, the first filter 316 blocks wavelengths between 725 nm and 800 nm. In some embodiments, the first filter 316 may be removable from the lens assembly 132. The first filter 316 may be used in imaging modalities such as Indocyanine Green (ICG) or OTL-38 (OTL) fluorescence imaging modalities to block illumination wavelengths between 725 nm and 800 nm that are used to stimulate the fluorescence. While the wavelengths between 725 nm and 800 nm are filtered out, the transmitted light may nonetheless contain additional spectrally distinct portions of light or, in other words, wavelengths of light other than those between 725 nm and 800 nm. For example, the transmitted light may include fluorescence wavelengths as well as visible light wavelengths, which may be individually separated by the prism assembly 137 as discussed in further detail below.

The lens assembly 132 may, in some embodiments, condition the light 302, such that conditioned light 304 passes into the prism assembly 137 and is ultimately focused on image sensor 332. The prism assembly 137 includes a first prism 320 that receives the conditioned light 304. Between the first prism 320 and a second prism 340 is a first dichroic beam splitter or spectral filter 324, which may be disposed on a surface of first prism 320 or the second prism 340. The dichroic beam splitter 324 filters and/or reflects different wavelengths of light, creating a cutoff between different spectral bands. For example, first dichroic beam splitter 324 may transmit light with wavelengths below 500 nm and above 650 nm, while reflecting light with wavelengths between 500 nm and 650 nm. As another example, the first dichroic beam splitter 324 may reflect light with wavelengths below 500 nm and above 650 nm, while transmitting light with wavelengths between 500 nm and 650 nm. As a result, the spectral band with wavelengths between 500 nm and 650 nm pass out of the first prism 320 as transmitted light 336, while the remaining spectral bands remain in the first prism 320 as reflected light 328. It should be noted that while a dichroic beam splitter is utilized in preferred embodiments, this is not limiting, and other splitting configurations are also envisioned. For example, the dichroic beam splitter 324 could be replaced by a half silvered mirror which splits the beam at some other proportion (for example, 50-50), and then splitter could then be followed by one or more filters, to filter out the undesired wavelength bands of each split beam. This is of course less desirable than preferred embodiments, due to the light intensity unnecessarily lost, as well as other considerations.

The reflected light 328 may be bent by or reflected inside the first prism 320 until the reflected light 328 passes into a first region 356 of an image sensor 332. The image sensor 332 may receive the reflected light 328 and photosensitive elements (e.g., photodiodes, pixels) within the first region 356 of the image sensor 332 may generate corresponding electric signals. In some embodiments, the electric signals may be passed to one or more other components of the system 100 (such as to the controller 108) and further used to generate one or more images. While FIG. 3A illustrates the image sensor 332 positioned approximately parallel to the conditioned light 304 (e.g., the image sensor 332 is in a horizontal position), the image sensor 332 may also be positioned approximately orthogonal to the conditioned light 304 (e.g., the image sensor 332 is in a vertical position) as shown in FIG. 3B. Notwithstanding the foregoing, the orientation of the image sensor 332 relative to any one or more components of the camera head 116 is in no way limited, and the image sensor 332 may be positioned differently depending on, for example, the type of endoscope or exoscope used, the type of surgical procedure, manufacturer specifications, design requirements, combinations thereof, and the like.

The first region 356 of the image sensor 332 may have a color filter array 334 capable of receiving one or more wavelengths of light, such as visible light (e.g., red light, blue light, and green light), infrared light, combinations thereof, and the like. In some embodiments, the CFA 334 may be so positioned as to enable photodiodes arranged in an array capture different wavelengths of light. For example, the CFA 334 may be a Bayer filter arranged in a Bayer pattern (e.g., a filter pattern with half green, one quarter red, and one quarter blue color filters). In some embodiments, the image sensor 332 may include four spectrally distinct spectral channels: a red light channel, a blue light channel, a green light channel, and an infrared light channel. Each channel may be used to determine pixel values when reconstructing one or more images of the surgical site. The channels of each image sensor region are defined, at least in part, by the CFA 334 positioned between the prism assembly 137 and the image sensor 332. In some embodiments the image sensor 332 may have three spectrally distinct spectral channels: a blue light channel, a green light channel, and a channel capable of detecting a combination of both red light and infrared light. In some embodiments, the image sensor 332 may be used to measure light with wavelengths reflected by the first dichroic beam splitter 324 (e.g., light with wavelengths below 500 nm and above 650 nm).

The CFA 334 may filter the reflected light 328 into multiple spectral channels. Each spectral channel (also referred to herein as a color channel) may have a range of wavelengths to which the channel is sensitive, such that each spectral channel is distinct from the other spectral channels on the CFA 334. For example, as shown in FIG. 3A, the reflected light 328 may pass through the CFA 334 and onto the first region 356 of the image sensor 332 in the form of three spectral channels: a red light channel, a blue light channel, and a green light channel. It is to be understood that, while the CFA 334 is shown as being disposed separate from the image sensor 332, this is for illustrative purposes only, and the space between the CFA 334 and the image sensor 332 may be minimal. With reference to both FIG. 3A and FIGS. 5A and 5C, the red light channel may see the range of wavelengths of light represented by the traces/lines 504 due to the red light channel's sensitivity to such wavelengths. Similarly, the blue light channel may see the range of wavelengths of light represented by the traces/lines 512, and the green light channel may see the range of wavelengths of light represented by the traces/lines 508. The wavelengths seen by each color channel may be measured by the first region 356 of the image sensor 332 and used in image processing to generate an image, as is known in the art.

The transmitted light 336 may pass through the first dichroic beam splitter 324 and may enter a second prism 340 and a third prism 348. The second prism 340 and the third prism 348 may bend and/or reflect the transmitted light 336 through a further optical conditioning element 352 and onto a second region 360 of the image sensor 332. The further optical conditioning element 352 may be, for example, a transparent optical element with an index of refraction selected in order to achieve a common focus onto image sensor 332 of both reflected light 328 and transmitted light 336. In some preferred embodiments, the second region 360 may be similar to the first region 356, that is, the entire image sensor 332 will comprise a single CFA, however this is not limiting. For example, in some embodiments the second region 360 may comprise a CFA different from that of the first region, capable of receiving one or more wavelengths of light, such as visible light, infrared light, combinations thereof, and the like. The second region 360 may comprise a filter arranged in a Bayer pattern, or another filter arrangement, other such arrangements enabling the second region 360 to collect four spectrally distinct spectral channels: a red light channel, a blue light channel, a green light channel, and an infrared light channel. In other embodiments, the second region 360 may comprise three spectrally distinct channels: a blue light channel, a green light channel, and a channel capable of detecting a combination of red light and infrared light. In one embodiment, the second region 360 of the image sensor 332 may be used to detect light with wavelengths between 500 nm and 650 nm.

As noted above, each spectral or color channel of the CFA 334 may have a range of wavelengths to which the channel is sensitive, such as a blue channel, a green channel, and a red channel. It should be understood that, while the first region 356 and the second region 360 may have three or more distinct spectral channels that are identical to one another (such as when the image sensor 332 has a single CFA 334), the spectral content (e.g., the range of wavelengths) of the light transmitted onto the first region 356 can be different than the spectral content (e.g., the range of wavelengths) of the light transmitted onto the second region 360 due to, for example, the filtering performed by the components of the imaging assembly 136, including the dichroic filter 324. For example, with reference to both FIG. 3A and FIGS. 5A and 5D, the red light channel of the second region 360 of the image sensor 332 may see the range of wavelengths of light represented by the traces/lines 516 due to the red light channel's sensitivity to such wavelengths. Similarly, the blue light channel of second region 360 of the image sensor 332 may see the range of wavelengths of light represented by the traces/lines 524, and the green light channel of the second region 360 of the image sensor 332 may see the range of wavelengths of light represented by the traces/lines 520. Due to the difference in spectral content (e.g., different ranges of wavelengths of light) and the presence of three distinct spectral channels on the CFA 334, the image sensor 332 may be able to receive and process up to six distinct spectral bands. Stated differently, the first region 356 can receive at least three spectral bands from the color channels of the CFA 334, and the second region 360 can also receive the spectral bands from the color channels of the CFA 334, but with distinct spectral bands from those seen by the first region 356. Since the spectral bands received by the first region 356 can be different from those received at the second region 360 (e.g., due to the different wavelengths of light incident on the CFA 334 in the first region 356 as compared to the second region 360), the image sensor 332 can receive up to six distinct spectral bands for image processing. This beneficially enables multiple imaging modalities with the use of a single image sensor.

In some embodiments, both the first region 356 and the second region 360 of the image sensor 332 may include three distinct spectral channels: a red light channel, a blue light channel, and a green light channel. In such embodiments, the red light channel on the first region 356 and/or the second region 360 may also be sensitive to infrared light. As a result, the first region 356 and/or the second region 360 of the image sensor 332 may be able to detect blue, green, and infrared spectral channels.

For illustrative purposes only, the following are examples of methods of preforming various imaging modalities using the camera head 116 as well as other components of the system 100.

In a "white light imaging" modality, the light source 112 and the camera head 116 may provide for imaging of a surgical scene using white light. The white light may be output either from the first illuminant 204, or from a combination of green light, blue light, and red light output from the first illuminant 204, second illuminant 208, and fifth illuminant 220, respectively. In such cases, the third illuminant 212 and the fourth illuminant 216 may be turned off or disabled, such that the combined light output 244 contains only white light. In some embodiments, the first illuminant 204 may emit white light while the second illuminant 208 and the fifth illuminant 220 each also emit blue and red light, respectively. In other words, all three of the first illuminant 204, the second illuminant 208 and the fifth illuminant 220 may emit light in the white light modality. Once the light is emitted from the light source 112, the light may illuminate the surgical scene. Light reflected from elements of the scene, light scattered from surfaces, fluorescent light emitted from fluorophores, light directly coming from other illumination sources, and the like may pass into the camera head 116 and, more specifically, into the lens assembly 132. The lens assembly 132 may then condition and/or direct the light (e.g., conditioned light 304) into the prism assembly 137 of the imaging assembly 136.

In embodiments where the "white light imaging" modality is enabled, the first region 356 of the image sensor 332 may capture light with wavelengths below 500 nm as well as light with wavelengths above 650 nm as directed thereto by the beam splitter 324, while the second region 360 of the image sensor 332 may capture light with wavelengths between 500 nm and 650 nm. The measurements from the first region 356 and/or the second region 360 of the image sensor 332 may be processed by the processor 120 to generate a true color image. In some embodiments, the processor 120 may use one or more algorithms (e.g., an image reconstruction algorithm, bilinear interpolation, gradient direction interpolation algorithms, etc.) to process the color channels on the first region 356 and/or the second region 360 of the image sensor 332 to generate the true color image. In one embodiment, the green and blue light channels (e.g., the spectral channels that detect green and blue light, respectively) of the first region 356 of the image sensor 332 and the red, green, and blue light channels of the second region 360 of the image sensor 332 may be used in reconstructing the true color image.

As another illustrative example, the imaging device 104 may operate in an ICG/OTL fluorescence with simultaneous white light imaging mode. In this mode, the white light may be generated similarly to as described above in white light mode, however, in addition the fourth illuminant 216 may also be enabled such that infrared light is included in the combined light output 244 of the light source 112. The wavelength or range of wavelengths emitted by the fourth illuminant being selected as it corresponds to the excitation wavelength of a target fluorophore. The combined light output 244 may then illuminate the surgical scene, and light reflected from elements of the scene, light scattered from surfaces, fluorescent light emitted from fluorophores, light directly coming from other illumination sources, and the like may be captured by the camera head 116. In this case, the ICG/OTL fluorescence may occur at a different wavelength of infrared light (e.g., above 800 nm wavelengths) than the infrared light generated by the light source 112 (e.g., about 770 nm). However, the direct infrared light generated by the fourth illuminant 216 may be blocked by the first filter 316 before reaching the prism assembly 137. The true color image may be created using the same color channels of the first region 356 and the second region 360 of the image sensor 332 as described above in the white light imaging mode, while the ICG/OTL fluorescence based on the infrared spectral band is detected by the infrared channel of the first region 356 of the image sensor 332. The channel measurements of the first region 356 and the second region 360 of the image sensor 332 may be sent to the processor 120, which may use one or more algorithms to generate an image of the surgical scene. The image of the surgical scene may include both a white light image and an overlaid image representing the fluorescence image collected. Generally, the combined image is represented as a false color image of the fluorescence image overlaid with the white light image, as is known in the art.

Figure 5A:
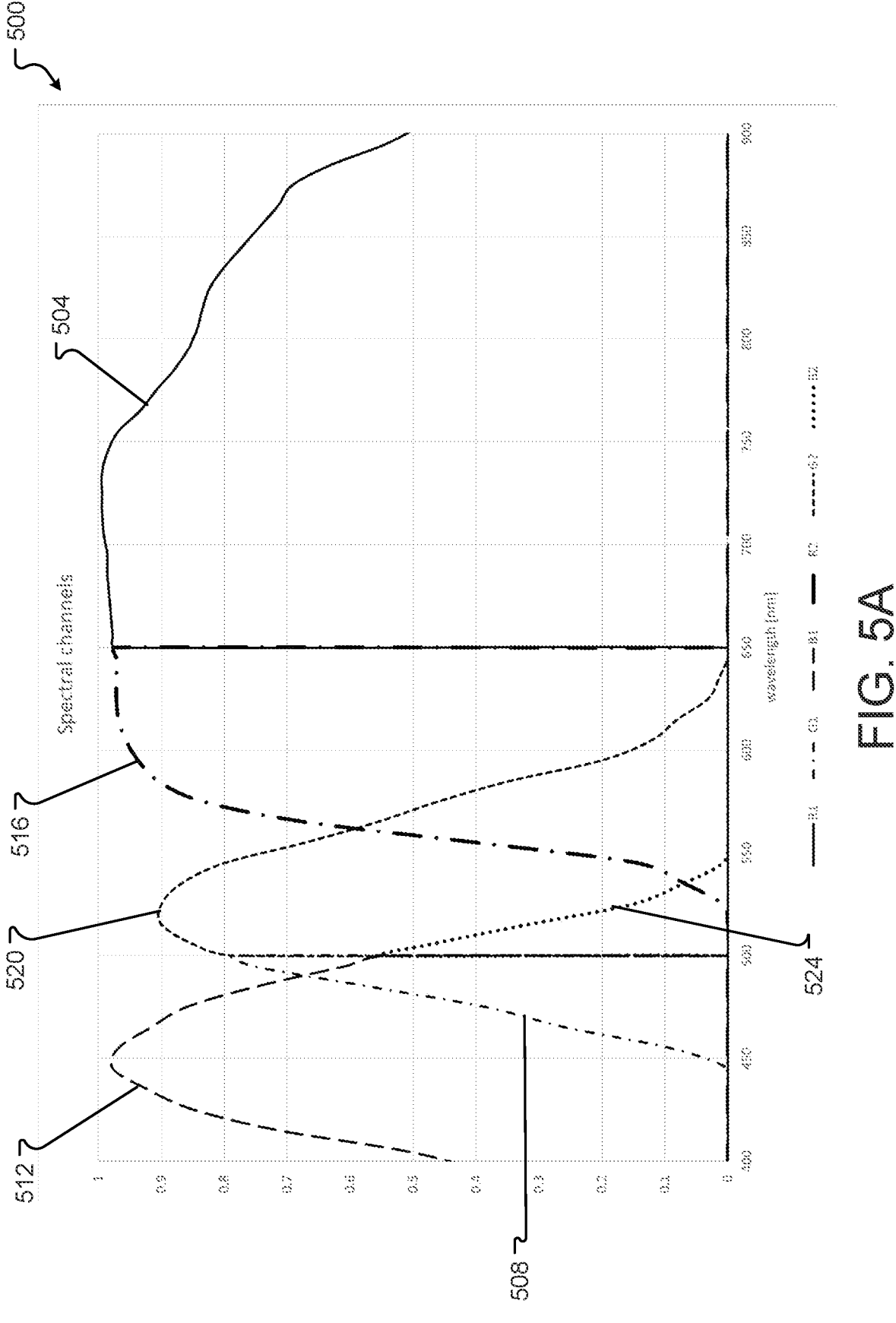
FIG. 5A shows the three spectral channel sensitivities and associated six spectral bands according to at least one exemplary embodiment.

FIGS. 5A-5D illustrate the channel sensitivities of one or more exemplary embodiments of the imaging assembly 136 (and more generally the camera head 116) shown in FIGS. 3A and 3B with a configuration described above, wherein the image sensor 332 is an RGB image sensor with a standard Bayer type CFA 334, and the image sensor 332 includes a first region 356 and a second region 360. FIG. 5A illustrates the complete spectrum sensitivity 500 for all channels represented across both regions of the image sensor. The blue sensors' sensitivity is represented by the curve indicated as 512 and 524. The green sensors' sensitivity is represented by the curve indicated as 508 and 520. Finally, the red sensors' sensitivity is represented by curve indicated as 516 and 504. As discussed previously the first dichroic beam splitter 324 in this example reflects light of wavelengths shorter than 500 nm and longer than 650 nm and directs this reflected light 328 to the first region 356 of the image sensor 332.

Figure 5B:
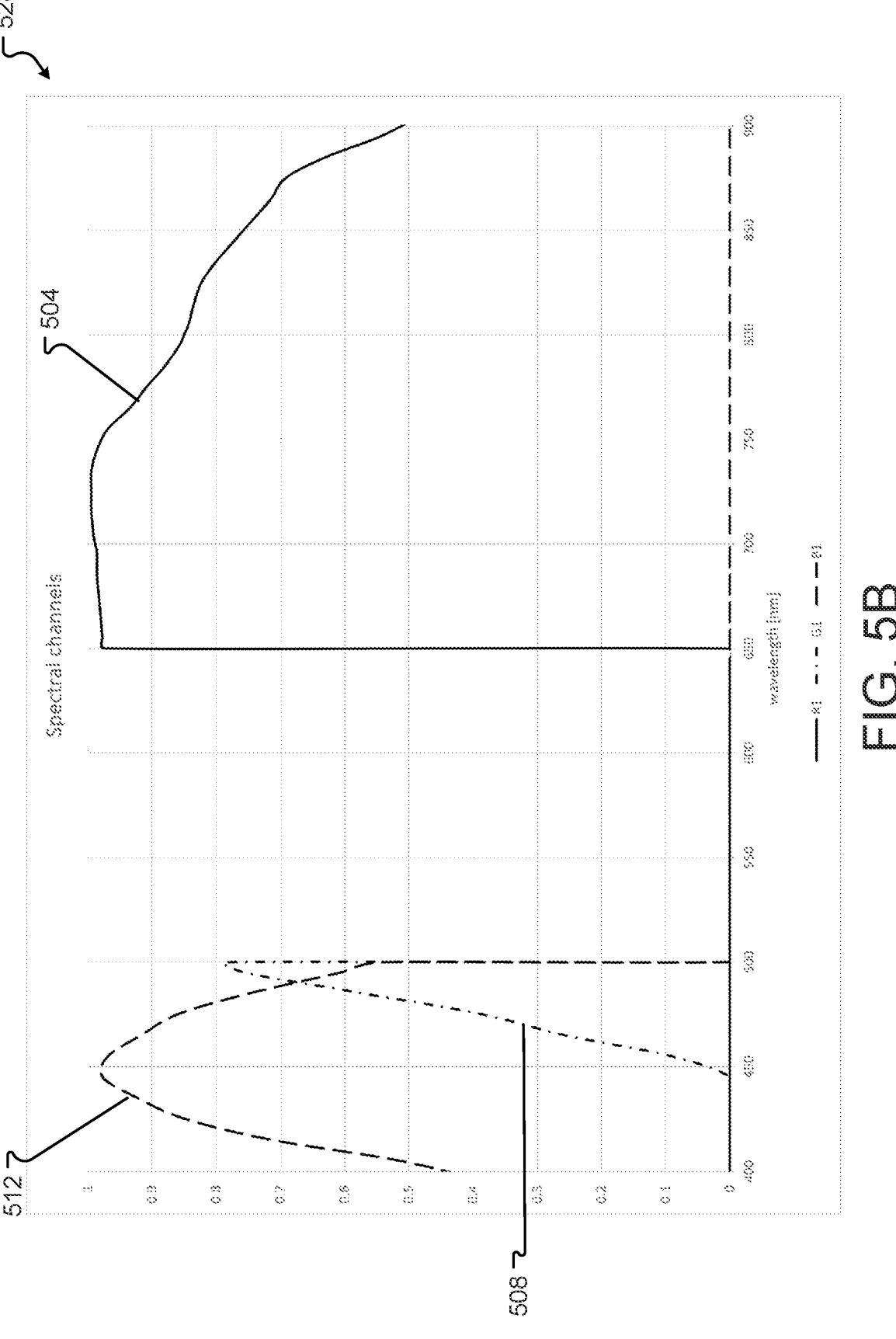
FIG. 5B shows the three spectral channel sensitivities of a first region of a single chip according to the at least one exemplary embodiment.

FIG. 5B illustrates the sensitivity 528 of the red, blue, and green channels of the first region 356 of the image sensor 332 with respect to this reflected light 328. The trace 512 shows the sensitivity of the blue channel, the trace 508 shows the sensitivity of the green channel, and the trace 504 shows the sensitivity of the red channel. The region between 500 nm and 650 nm shows no sensitivity, of course, as light in that spectral band has been directed by the dichroic beam splitter 324 to the second region. It should be noted that the sensitivity as depicted by the trace 504 of the red channel extends well into the near infrared (NIR) spectral band, and is thus sensitive to NIR radiation, which is of particular interest for some fluorescence imaging applications, such as those employing ICG, as its emission peak is within this range.

Figure 5C:
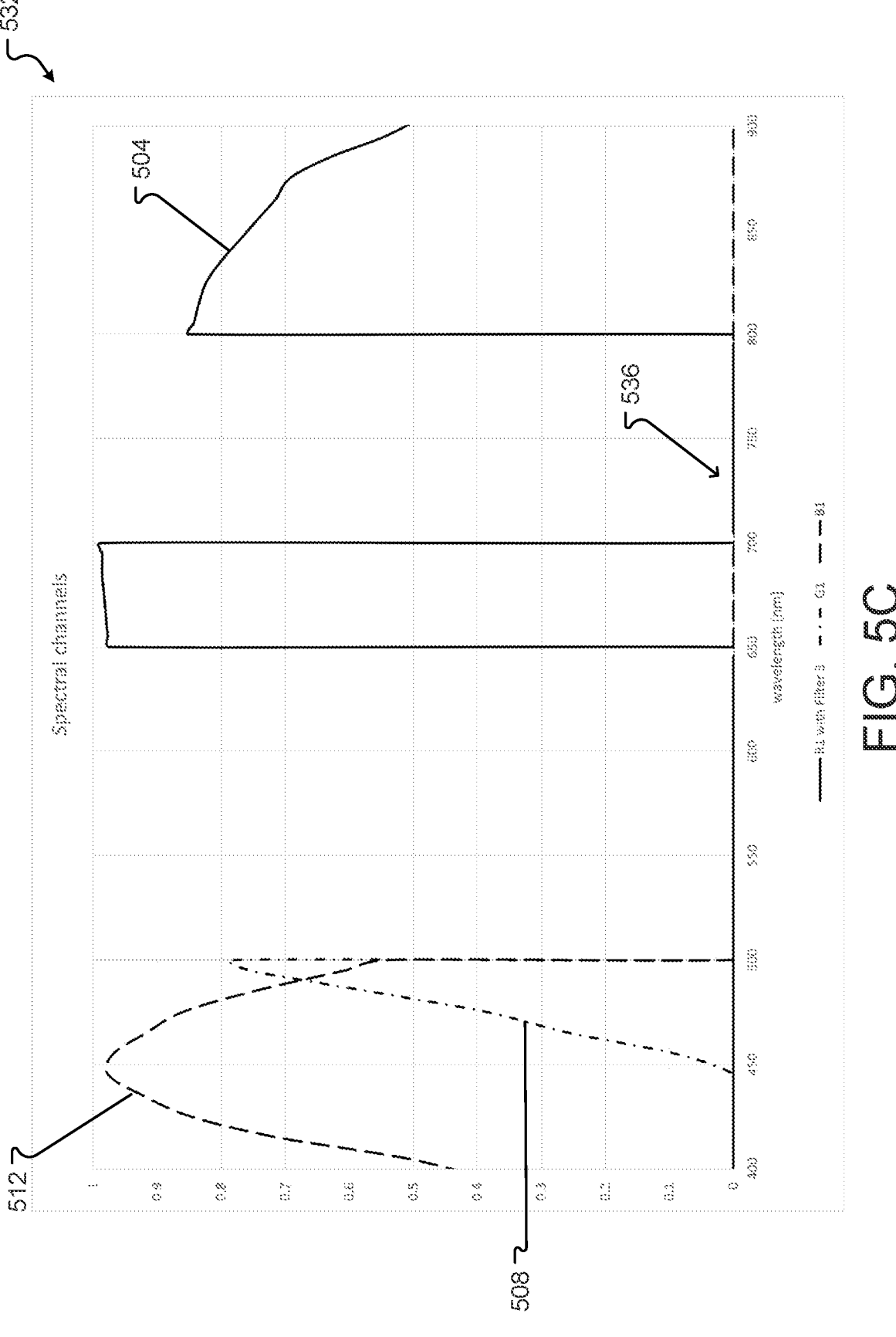
FIG. 5C shows the three spectral channel sensitivities of the first region of the at least one exemplary embodiment wherein the optical system includes a filter to block excitation light between 700 and 800 nm.

FIG. 5C illustrates the sensitivity 532 of the three RGB channels of the first region 356 of the image sensor 332 when the first filter 316 is an element of the lens assembly 132 of the camera head 116, and blocks light representing the excitation range of, for example, ICG, that is, light between 700 nm and 800 nm. Thus, the sensitivity 504 of the red channel, when this excitation band is blocked, now shows a notch 536 as the range of wavelengths of the reflected light 328 will not contain any light in this spectral band, as it has been previously blocked by the optical system. Thus, when operating in ICG mode, the only light detected by the red channel of first region 356 of the image sensor 332 will be a NIR signal corresponding to the ICG emission light, as the excitation light has been blocked by the first filter 316 and the light source 112 does not emit any light in the 650-700 nm range when operated in this mode.

When operating in CY5/CY5.5 mode the red channel of the first region 356 of the image sensor is used to detect the emission of these fluorophores which occurs in the 650-700 nm spectral band. Further, this embodiment can take advantage of the sensitivity in this range when operated in a "white light imaging mode," when the imaging system is used in conjunction with a conventional, white light source, rather than that shown in FIG. 2. In this case, the first region 356 of the image sensor will then generate blue, green, and red signals, and the combined signals from the first and second regions of the image sensor can yield a fuller spectrum image.

Figure 5D:
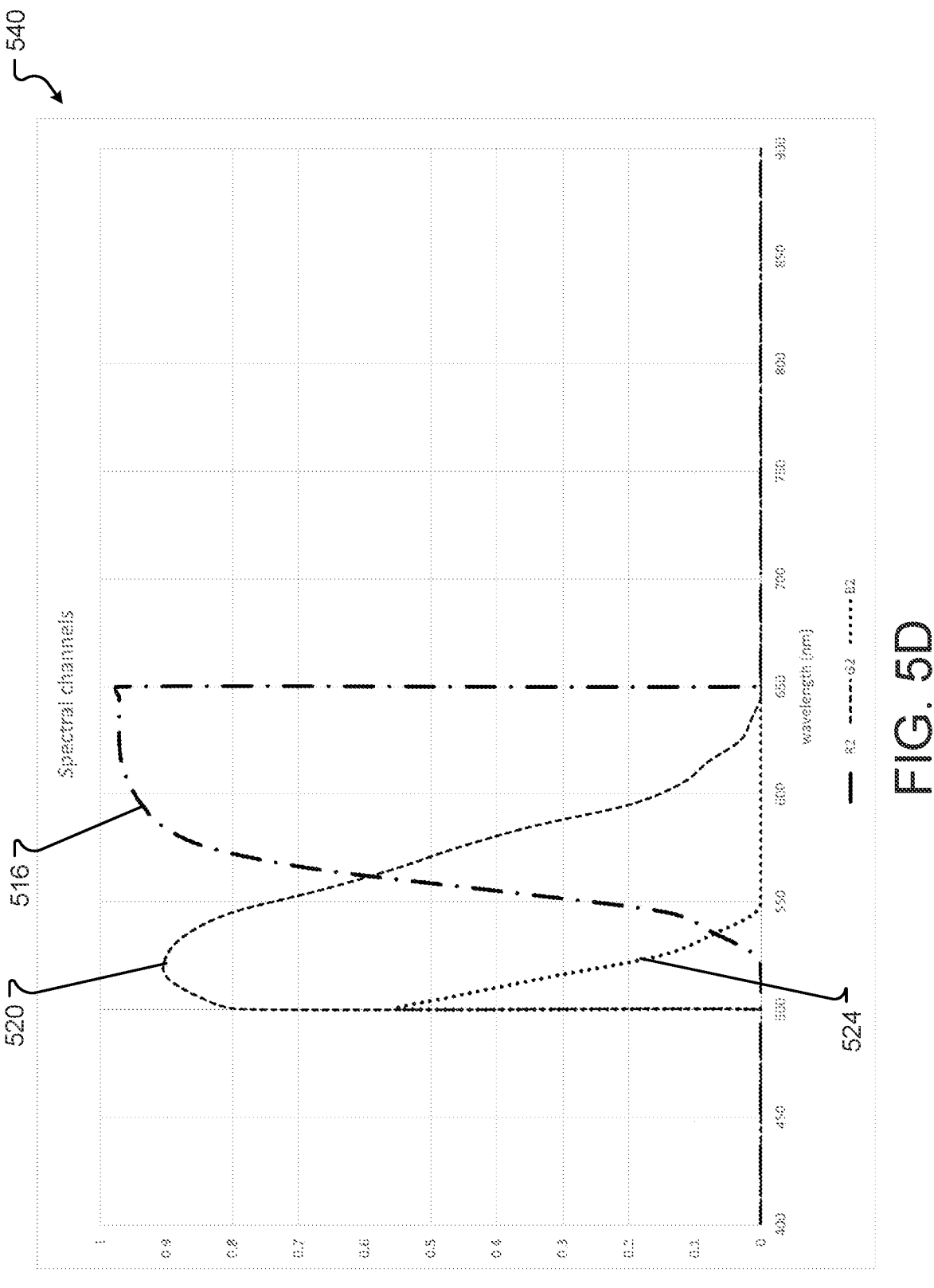
FIG. 5D shows the three spectral channel sensitivities of a second region of a single chip according to the at least one exemplary embodiment.

FIG. 5D illustrates the sensitivity 540 of the three RGB channels of the second region 360 of the image sensor 332 to the light transmitted 336 by the dichroic beam splitter 324 within the wavelength range of 500-650 nm. Here we can see the sensitivity 524 of the blue channel, the sensitivity 520 of the green channel, and the sensitivity 516 of the red channel. We thus see the six distinct spectral bands received by the two distinct regions of the image sensor, in this case, two blue spectral bands, two green spectral bands, one red spectral band, and one spectral band that will operate in the red band or NIR band, depending on the mode of operation. The image data thus received by the six distinct spectral bands in this exemplary embodiment can be used to generate a white light, as well as provide a fluorescence image overlay.

As another illustrative example, the imaging device 104 may operate in an oxygenation/perfusion with simultaneous white light imaging mode. In this mode, the first illuminant 204, the second illuminant 208, and the fifth illuminant 220 may together generate white light and, the fifth illuminant 220 may generate a discrete red light spectrum centered at a wavelength of 630 nm. Further, the third illuminant 212 may generate infrared light spectrum centered at a wavelength of about 940 nm. As the fifth illuminant 220 generates red light spectrum centered at 630 nm and the third filter 232 blocks light with wavelengths greater than 650 nm, light in the combined light output 244 may not include light with wavelengths greater than 650 nm, other than the 940 nm infrared light. The light entering the prism assembly 137 may be directed toward the first region 356 and the second region 360 of the image sensor 332 in the manner discussed above, and a true color white image may be generated based on the green and blue light channels of the first region 356 of image sensor 332 and the red, green, and blue light channels of the second region 360 of the image sensor 332. Perfusion is determined by comparing the red light channel data from the second region 360 of the image sensor 332 with the 940 nm signal captured by the infrared light channel in the first region 356 of the image sensor 332 using one or more algorithms known in the art. Based on the comparison, a perfusion image may be generated.

In another illustrative example, the imaging device 104 may operate in a Cyanine-5 (Cy5) or Cy5.5 fluorescence with simultaneous white light imaging mode. In this mode, the light source 112 may produce white light, with the red light spectrum generated by a discrete red source with a center at a wavelength of 630 nm. Due to the position of the third filter 232, the combined light output 244 may have no light with wavelengths longer than 650 nm. Reflected light off the surgical scene may then be directed through the lens assembly 132 to the prism assembly 137. A white light image may be generated based on the green and blue light channels of the first region 356 of the image sensor 332 and the red, blue, and green light channels of the second region

360 of the image sensor 332. The fluorescence image may be generated based on the red light channel of the first region 356 of the image sensor 332.

In yet another illustrative example, the imaging device 104 may operate in a fluorescein fluorescence with simultaneous greyscale imaging mode. In this mode, the light source 112 may output a combined light 244 that includes blue light and that contains no wavelengths longer than 500 nm. In other words, green and red light may be absent from the combined light 244. In some optional embodiments, the combined light output 244 may also contain wavelengths longer than 650 nm (e.g., near-infrared or infrared light). The light reflected from the surgical scene may be received by the camera head 116, and a greyscale image may be created based on all color channels of the first region 356 of the image sensor 332 (e.g., the blue, green, red, and infrared light channels). Additionally, the green and blue channels of the second region 360 of the image sensor 332 may be used to generate a fluorescein fluorescence image.

Figure 4:
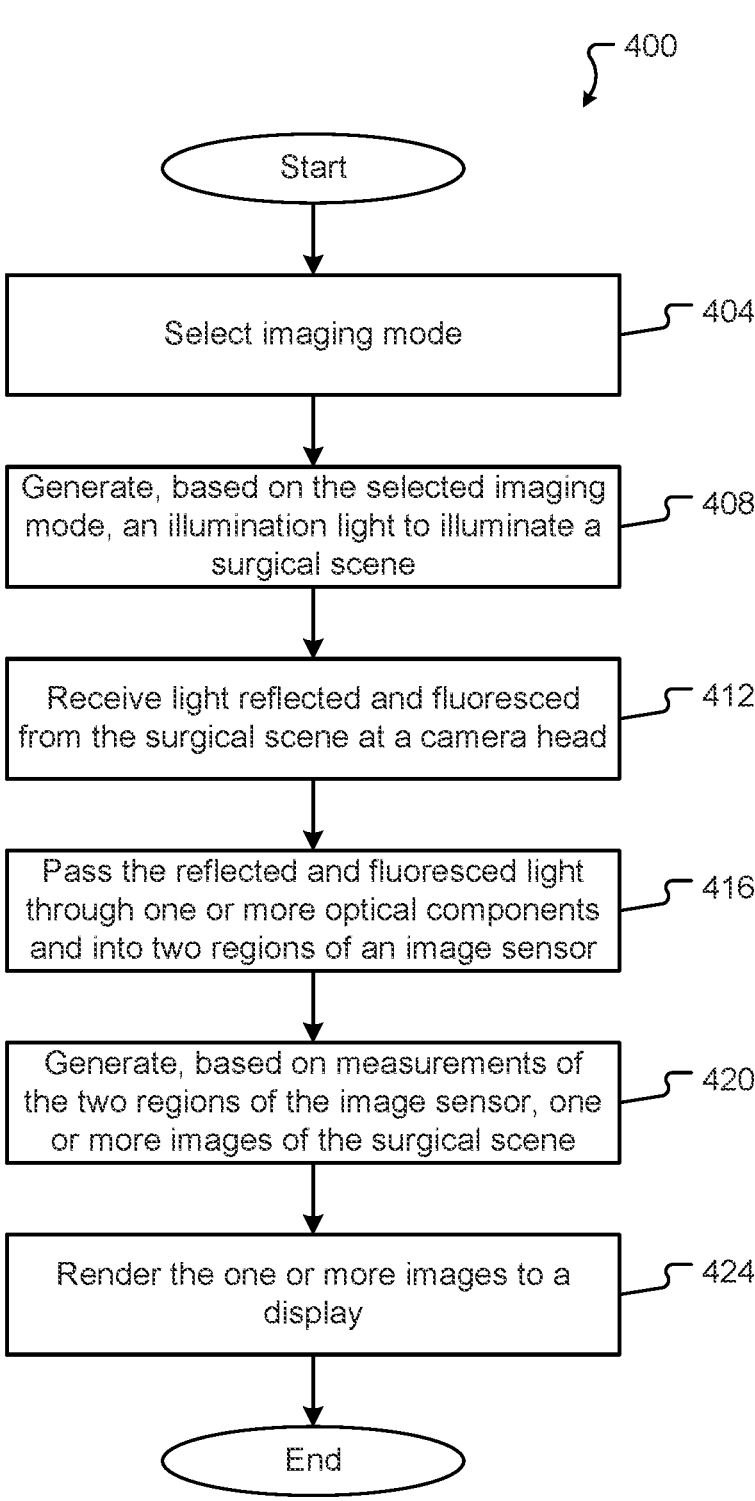
FIG. 4 shows a method according to at least one exemplary embodiment.

FIG. 4 shows a method 400 according to at least one exemplary embodiment of the present disclosure. The method 400 may be used, for example, to select and generate one or more images for a selected image modality.

The method 400 starts and then proceeds to step 404, where an imaging mode is selected. The imaging mode may be a white light imaging mode, an ICG/OTL fluorescence mode, an oxygenation/perfusion mode, a Cy5/Cy5.5 fluorescence mode, a fluorescein fluorescence mode, and the like. The mode may be chosen based on a physician input (e.g., the physician selects the mode by pressing a virtual button on a screen rendered on the display 148).

The method 400 then continues to step 408, wherein a light source comprising a plurality of illuminants generates an illumination light to illuminate a surgical scene, where the illuminants activated are determined by the selected imaging mode. The light source may be similar to or the same as the light source 112. The controller 108 may determine, based on the physician input and using instructions and/or algorithms 128, one or more illuminants that should be enabled to generate the required illumination. For example, in a white light mode, the controller 108 may determine that the first illuminant 204, the second illuminant 208, and the fifth illuminant 220 should be enabled such that red, blue, and green light are generated, while also determining that the third illuminant 212 and the fourth illuminant 216 should not be enabled. In another example, in an oxygenation/perfusion mode, the controller 108 may determine that the first illuminant 204, the second illuminant 208, and the fifth illuminant 220 should be enabled, and that the third illuminant 212 (which generates infrared light at 940 nm) should also be enabled. Once the illuminants are enabled or disabled, the controller 108 may cause the illuminants to emit light, such that the light source 112 illuminates the surgical scene with the light required by the imaging mode.

The method 400 then continues to step 412, where light reflects and/or fluoresces from the surgical scene and is captured at a camera head, such as the camera head 116. The method 400 then continues to step 416, where the reflected and/or fluoresced light is passed through one or more optical components, such as the lens assembly 132, and into the prism assembly 137 of the imaging assembly 136 (e.g., in the form of conditioned light 304). The light may be split by one or more beam splitters, such as a beam splitting prism which may comprise selective spectral filters (e.g., filters designed to filter out a range of wavelengths of light), with transmitted and reflected light being passed to different regions of an image sensor.

The method 400 then continues to step 420 where one or more images are generated based on the measurements from the two distinct regions of the image sensor. The number and types of images be based on the current imaging mode of the camera head. For instance, during white light mode, a true color image may be generated based on the color channels of the two distinct regions of the image sensor. As another example and when the camera head is in the ICG mode, ICG fluorescence images may be generated based on detected infrared light. The number and type of images generated is in no way limited, and any image discussed herein may be generated in the step 420. The controller 108 may be used along with the instructions 128 to access and implement one or more image processing algorithms to transform the data received from the two distinct regions (e.g., from a first region and a second region) of the image sensor into corresponding images.

The method 400 then continues to step 424, where the one or more images are rendered to a display. The display may be similar to or the same as the display 148. In some embodiments, the one or more images may be captured in the form of a video by repeatedly looping back after step 424 to step 412 and thus repeating steps 412, 416, 420, and 424 for each successive video frame. In such a video display the camera head generally continuously receives light, and images are continuously generated from the sensor measurements. The method 400 then ends. In some embodiments, the method 400 may then repeat during the course of the surgery or surgical procedure as different imaging modalities are used, for example, by repeating step 404 and selecting a different imaging mode.

Any of the steps, functions, and operations discussed herein can be performed continuously and automatically.

While the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as a server, communication device, or collocated on a particular node of a distributed network, such as an analog and/or digital telecommunications network, a packet-switched network, or a circuit-switched network. It will be appreciated from the preceding description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire, and fiber optics, and may take the form of acoustic or light waves, such as those generated during radio-wave and infra-red data communications.

While the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the present disclosure includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the embodiments with reference to particular standards and protocols, the disclosure is not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various embodiments, configurations, and aspects, includes components, methods, processes, systems and/or apparatus substantially as depicted and described herein, including various embodiments, sub-combinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

Example aspects of the present disclosure include:

An endoscopic or exoscopic imaging device according to at least one embodiment of the present disclosure comprises: an optical element configured to separate an input light into at least a first spectrally distinct portion of output light and a second spectrally distinct portion of output light; and an image sensor with a color filter array (CFA), the image sensor positioned so as to receive light from the first spectrally distinct portion of output light at a first region of the image sensor and to receive light from the second spectrally distinct portion of output light at a second region of the image sensor, wherein the CFA is configured to receive the first portion of output light and the second portion of output light incident thereon and filter the first portion of output light and the second portion of output light into at least six resulting spectral channels that are spectrally distinct from one another, a first, second, and third spectral channel collected by the first region of the image sensor, and a fourth, fifth, and sixth spectral channel collected by the second region of the image sensor.

Any of the aspects herein, wherein a first wavelength of light is present in at least two of the first, second, and third spectral channels collected by the first portion of the image sensor and/or at least two of the fourth, fifth, and sixth spectral channels collected by the second portion of the image sensor.

Any of the aspects herein, wherein a first wavelength of light is not present in at least two of the first, second, and third spectral channels collected by the first portion of the image sensor and/or at least two of the fourth, fifth, and sixth spectral channels collected by the second portion of the image sensor.

Any of the aspects herein, wherein the at least six resulting spectrally distinct spectral channels of the CFA comprise a combined red light and infrared light channel, a green light channel, and a blue light channel.

Any of the aspects herein, wherein the at least six resulting spectrally distinct spectral channels of the CFA comprise a red light channel, a green light channel, a blue light channel, and an infrared light channel.

Any of the aspects herein, further comprising a first spectral filter that is configured to filter out a range of wavelengths of the input light.

Any of the aspects herein, wherein the optical element is configured to separate the input light by means of a dichroic beam splitter reflecting light with wavelengths shorter than 500 nanometers (nm), reflecting light with wavelengths longer than 650 nm, and transmitting light with wavelengths between 500 nm and 650 nm.

Any of the aspects herein, wherein the optical element is configured to separate the input light by means of a dichroic beam splitter reflecting light with wavelengths between 500 nanometers (nm) and 650 nm, transmitting light with wavelengths shorter than 500 nm, and transmitting light with wavelengths longer than 650 nm.

Any of the aspects herein, wherein the first spectral filter blocks a wavelength band that corresponds to a fluorescence excitation signal.

Any of the aspects herein, further comprising: an illumination device that illuminates a scene to be imaged with light comprising a first set of wavelengths.

Any of the aspects herein, wherein the illumination device provides white light with wavelengths between about 450 nanometers (nm) and about 650 nm, and wherein a white light image is created from a blue light channel and a green light channel of the first region of the image sensor, and from a blue light channel, a green light channel, and a red light channel of the second region of the image sensor.

Any of the aspects herein, wherein the illumination device generates an illumination that comprises a red spectral band centered at about 630 nanometers (nm) and an infrared spectral band centered at about 940 nm, and wherein an oxygenation or perfusion image is created based on at least an infrared light channel of the first region of the image sensor, and also based on a red light channel of the second region of the image sensor.

Any of the aspects herein, wherein the illumination device generates an illumination with wavelengths between about 725 nanometers (nm) and about 800 nm, and wherein an ICG or OTL fluorescence image is imaged onto the first region of the image sensor.

Any of the aspects herein, wherein the illumination device generates an illumination that comprises a red spectral band centered at about 630 nanometers (nm), and wherein a Cy5 or a Cy5.5 fluorescence image is imaged onto the first region of the image sensor.

Any of the aspects herein, wherein the illumination device generates illumination that includes a blue spectral band of with wavelengths between about 450 nanometers (nm) and about 500 nm, wherein a greyscale image is created from the illumination that is imaged onto the first region of the image sensor, and wherein a fluorescein fluorescence image is imaged onto the second region of the image sensor.

Any of the aspects herein, wherein the illumination comprises a spectral component with a wavelength longer than 650 nm, wherein the spectral component is imaged onto the first region of the image sensor, and wherein a partially colored image is created from one or more color channels of the first region of the image sensor.

An endoscopic or exoscopic imaging system according to at least one embodiment of the present disclosure comprises: an optical element configured to separate input light into at least a first spectrally distinct portion of output light and a second spectrally distinct portion of output light that are directed to at least two discrete regions of an image sensor; a processor; and a memory storing instructions thereon that, when processed by the processor, cause the processor to: detect, from a first region of the image sensor with a color filter array (CFA), the CFA configured to receive the first spectrally distinct portion of output light and the second spectrally distinct portion of light incident thereon and filter the first portion of output light and the second portion of output light into at least six resulting spectral channels that are spectrally distinct from one another, a first, second, and third band of light; and detect, from a second region of the image sensor with the CFA, a fourth, fifth, and sixth band of light.

Any of the aspects herein, wherein the at least six resulting spectrally distinct spectral channels comprise a combined red light and infrared light channel, a green light channel, and a blue light channel.

Any of the aspects herein, wherein the at least six resulting spectrally distinct spectral channels comprise a red light channel, a green light channel, a blue light channel, and an infrared light channel.

Any of the aspects herein, wherein an illumination device provides white light with wavelengths between about 450 nanometers (nm) and about 650 nm, and wherein a white light image is created from a blue light channel and a green light channel of the first region of the image sensor, and from a blue light channel, a green light channel, and a red light channel of the second region of the image sensor.

Any of the aspects herein, wherein an illumination device generates an illumination that comprises a red spectral band centered at about 630 nanometers (nm) and an infrared spectral band centered at about 940 nm, and wherein an oxygenation or perfusion image is created based on at least a combined red light and infrared light channel of the first region of the image sensor, and also based on a red light channel of the second region of the image sensor.

Any of the aspects herein, wherein an illumination device generates an illumination with wavelengths between about 725 nanometers (nm) and about 800 nm, and wherein an ICG or OTL fluorescence image is imaged onto the first region of the image sensor.

Any of the aspects herein, wherein an illumination device generates an illumination that comprises a red spectral band centered at about 630 nanometers (nm), and wherein a Cy5 or a Cy5.5 fluorescence image is imaged onto the first region of the image sensor.

Any of the aspects herein, wherein an illumination device generates fluorescein excitation illumination that includes a blue spectral band of with wavelengths between about 450 nanometers (nm) and about 500 nm, wherein a greyscale image is created from the fluorescein excitation illumination that is imaged onto the first region of the image sensor, and wherein a fluorescein fluorescence image is imaged onto the second region of the image sensor.

An endoscopic or exoscopic imaging system according to at least one embodiment of the present disclosure comprises: an optical element configured to separate an input light into at least a first spectrally distinct portion of output light and a second spectrally distinct portion of output light; an image sensor with a color filter array (CFA) disposed over a first region and a second region of the image sensor, the CFA configured to receive the first portion of output light and the second portion of output light incident thereon and filter the first portion of output light and the second portion of output light into at least six resulting spectral channels that are spectrally distinct from one another, a first, second, and third spectral channel collected by the first region of the image sensor, and a fourth, fifth, and sixth spectral channel collected by the second region of the image sensor; and an illumination device that illuminates a scene to be imaged with light containing a first set of wavelengths, wherein the imaging system is configured to operate in one or more imaging modes including one or more of: a white light imaging mode, an ICG or OTL mode, an oxygenation or perfusion mode, a Cy5 or Cy5.5 mode, and a fluorescein mode.

Any of the aspects herein, wherein a first wavelength of light is present in at least two of the first, second, and third spectral channels collected by the first portion of the image sensor and/or at least two of the fourth, fifth, and sixth spectral channels collected by the second portion of the image sensor.

Any of the aspects herein, wherein a first wavelength of light is not present in at least two of the first, second, and third spectral channels collected by the first portion of the image sensor and/or at least two of the fourth, fifth, and sixth spectral channels collected by the second portion of the image sensor.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

What is claimed is:

1. An endoscopic or exoscopic imaging device, comprising:

an optical element comprising a dichroic beam splitter configured to separate an input light into at least a first spectrally distinct portion of output light and a second spectrally distinct portion of output light, wherein the dichroic beam splitter is configured to either reflect light with wavelengths shorter than about 500 nm and longer than about 650 nm and transmit light with wavelengths between 500 nm and 650 nm, or is configured to reflect light between about 500 nm and about 650 nm and to transmit light with wavelengths shorter than about 500 nm and longer than about 650 nm; and an image sensor with a color filter array (CFA), the image sensor positioned so as to receive light from the first spectrally distinct portion of output light at a first region of the image sensor and to receive light from the second spectrally distinct portion of output light at a second region of the image sensor, wherein the CFA is configured to receive the first portion of output light and the second portion of output light incident thereon and filter the first portion of output light and the second portion of output light into at least six resulting spectral channels that are spectrally distinct from one another, a first, second, and third spectral channel collected by the first region of the image sensor, and a fourth, fifth, and sixth spectral channel collected by the second region of the image sensor.

2. The imaging device of claim 1, wherein a first wavelength of light is present in at least two of the first, second, and third spectral channels collected by the first portion of the image sensor and/or at least two of the fourth, fifth, and sixth spectral channels collected by the second portion of the image sensor.

3. The imaging device of claim 1, wherein a first wavelength of light is not present in at least two of the first, second, and third spectral channels collected by the first portion of the image sensor and/or at least two of the fourth, fifth, and sixth spectral channels collected by the second portion of the image sensor.

4. The imaging device of claim 1, wherein the at least six resulting spectrally distinct spectral channels of the CFA comprise a combined red light and infrared light channel, a green light channel, and a blue light channel.

5. The imaging device of claim 1, wherein the at least six resulting spectrally distinct spectral channels of the CFA comprise a red light channel, a green light channel, a blue light channel, and an infrared light channel.

6. The imaging device of claim 1, further comprising a first spectral filter that is configured to filter out a range of wavelengths of the input light.

7. The imaging device of claim 6, wherein the first spectral filter blocks a wavelength band that corresponds to a fluorescence excitation signal.

8. The imaging device of claim 1, further comprising:

an illumination device that illuminates a scene to be imaged with light comprising a first set of wavelengths; and a processor.

9. The imaging device of claim 8, wherein the illumination device is configured to provide white light with wavelengths between about 450 nanometers (nm) and about 650 nm, and wherein the processor is configured to generate a white light image from a blue light channel and a green light channel of the first region of the image sensor, and from a blue light channel, a green light channel, and a red light channel of the second region of the image sensor.

10. The imaging device of claim 8, wherein the illumination device is configured to generate an illumination that comprises a red spectral band centered at about 630 nanometers (nm) and an infrared spectral band centered at about 940 nm, and wherein the processor is configured to generate an oxygenation or perfusion image based on at least an infrared light channel of the first region of the image sensor, and also based on a red light channel of the second region of the image sensor.

11. The imaging device of claim 8, wherein the illumination device is configured to generate an illumination with wavelengths between about 725 nanometers (nm) and about 800 nm, and wherein an ICG or OTL fluorescence image is imaged onto the first region of the image sensor.

12. The imaging device of claim 8, wherein the illumination device is configured to generate an illumination that comprises a red spectral band centered at about 630 nanometers (nm), and wherein a Cy5 or a Cy5.5 fluorescence image is imaged onto the first region of the image sensor.

13. The imaging device of claim 8, wherein the illumination device is configured to generate an illumination that includes a blue spectral band of with wavelengths between about 450 nanometers (nm) and about 500 nm, wherein the processor is configured to generate a greyscale image from the illumination that is imaged onto the first region of the image sensor, and wherein a fluorescein fluorescence image is imaged onto the second region of the image sensor.

14. The imaging device of claim 13, wherein the illumination comprises a spectral component with a wavelength longer than 650 nm, wherein the spectral component is imaged onto the first region of the image sensor, and wherein the processor is configured to render a partially colored image from one or more color channels of the first region of the image sensor.

15. An endoscopic or exoscopic imaging system, comprising:

an optical element comprising a dichroic beam splitter configured to separate input light into at least a first spectrally distinct portion of output light and a second spectrally distinct portion of output light that are directed to at least two discrete regions of an image sensor, wherein the dichroic beam splitter is configured to either reflect light with wavelengths shorter than about 500 nm and longer than about 650 nm and transmit light with wavelengths between 500 nm and 650 nm, or is configured to reflect light between about 500 nm and about 650 nm and to transmit light with wavelengths shorter than about 500 nm and longer than about 650 nm;

a processor; and a memory storing instructions thereon that, when processed by the processor, cause the processor to:

receive a first image data, detected by a first region of the image sensor with a color filter array (CFA), the CFA configured to receive the first spectrally distinct portion of output light and the second spectrally distinct portion of light incident thereon and filter the first portion of output light and the second portion of output light into at least six resulting spectral channels that are spectrally distinct from one another, a first, second, and third band of light; and receive a second image data, detected by a second region of the image sensor with the CFA, a fourth, fifth, and sixth band of light.

16. The system of claim 15, wherein the at least six resulting spectrally distinct spectral channels comprise a combined red light and infrared light channel, a green light channel, and a blue light channel.

17. The system of claim 15, wherein the at least six resulting spectrally distinct spectral channels comprise a red light channel, a green light channel, a blue light channel, and an infrared light channel.

18. The system of claim 15, wherein an illumination device is configured to provide white light with wavelengths between about 450 nanometers (nm) and about 650 nm, and wherein the processor is configured to generate a white light image from a blue light channel and a green light channel of the first region of the image sensor, and from a blue light channel, a green light channel, and a red light channel of the second region of the image sensor.

19. The system of claim 15, wherein an illumination device is configured to generate an illumination that comprises a red spectral band centered at about 630 nanometers (nm) and an infrared spectral band centered at about 940 nm, and wherein the processor is configured to generate an oxygenation or perfusion image based on at least a combined red light and infrared light channel of the first region of the image sensor, and also based on a red light channel of the second region of the image sensor.

20. The system of claim 15, wherein an illumination device is configured to generate an illumination with wavelengths between about 725 nanometers (nm) and about 800 nm, and wherein an ICG or OTL fluorescence image is imaged onto the first region of the image sensor.

21. The system of claim 15, wherein an illumination device is configured to generate an illumination that comprises a red spectral band centered at about 630 nanometers (nm), and wherein a Cy5 or a Cy5.5 fluorescence image is imaged onto the first region of the image sensor.

22. The system of claim 15, wherein an illumination device is configured to generate fluorescein excitation illumination that includes a blue spectral band of with wavelengths between about 450 nanometers (nm) and about 500 nm, wherein the processor is configured to generate a greyscale image from the fluorescein excitation illumination that is imaged onto the first region of the image sensor, and wherein a fluorescein fluorescence image is imaged onto the second region of the image sensor.

23. An endoscopic or exoscopic imaging system, comprising:

an optical element comprising a dichroic beam splitter configured to separate an input light into at least a first spectrally distinct portion of output light and a second spectrally distinct portion of output light, wherein the dichroic beam splitter is configured to either reflect light with wavelengths shorter than about 500 nm and longer than about 650 nm and transmit light with wavelengths between 500 nm and 650 nm, or is configured to reflect light between about 500 nm and about 650 nm and to transmit light with wavelengths shorter than about 500 nm and longer than about 650 nm;

an image sensor with a color filter array (CFA) disposed over a first region and a second region of the image sensor, the CFA configured to receive the first portion of output light and the second portion of output light incident thereon and filter the first portion of output light and the second portion of output light into at least six resulting spectral channels that are spectrally distinct from one another, a first, second, and third spectral channel collected by the first region of the image sensor, and a fourth, fifth, and sixth spectral channel collected by the second region of the image sensor; and an illumination device that illuminates a scene to be imaged with light containing a first set of wavelengths, wherein the imaging system is configured to operate in one or more imaging modes including one or more of: a white light imaging mode, an ICG or OTL mode, an oxygenation or perfusion mode, a Cy5 or Cy5.5 mode, and a fluorescein mode.

24. The imaging system of claim 23, wherein a first wavelength of light is present in at least two of the first, second, and third spectral channels collected by the first portion of the image sensor and/or at least two of the fourth, fifth, and sixth spectral channels collected by the second portion of the image sensor.

25. The imaging system of claim 23, wherein a first wavelength of light is not present in at least two of the first, second, and third spectral channels collected by the first portion of the image sensor and/or at least two of the fourth, fifth, and sixth spectral channels collected by the second portion of the image sensor.

\* \* \* \* \*